(12) United States Patent
Rafter et al.

(10) Patent No.: US 6,425,869 B1
(45) Date of Patent: Jul. 30, 2002

(54) WIDEBAND PHASED-ARRAY TRANSDUCER FOR UNIFORM HARMONIC IMAGING, CONTRAST AGENT DETECTION, AND DESTRUCTION

(75) Inventors: Patrick G Rafter, Windham, NH (US); Jodi Lisa Tuck Perry, Methuen; Jie Chen, North Andover, both of MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 1 day.

(21) Appl. No.: 09/618,350

(22) Filed: Jul. 18, 2000

(51) Int. Cl.$^7$ ................................................ A61B 8/14
(52) U.S. Cl. ..................................................... 600/458
(58) Field of Search ................................ 600/441, 443, 600/447, 454, 458; 73/599, 602; 367/7, 11, 103, 105, 138

(56) References Cited

U.S. PATENT DOCUMENTS

| | | | |
|---|---|---|---|
| 5,410,516 A | | 4/1995 | Uhlendorf et al. .............. 367/7 |
| 5,558,092 A | | 9/1996 | Unger et al. ................. 128/660 |
| 5,740,128 A | | 4/1998 | Hossack et al. ............. 367/138 |
| 5,833,613 A | | 11/1998 | Averkiou et al. ............ 600/440 |
| 5,879,303 A | | 3/1999 | Averkiou et al. ............ 600/447 |
| 5,891,038 A | * | 4/1999 | Seyed-Bolorforosh et al. .. 600/447 |
| 5,951,478 A | * | 9/1999 | Hwang et al. ............... 600/443 |
| 6,027,448 A | * | 2/2000 | Hossack et al. ............. 600/447 |
| 6,064,628 A | * | 5/2000 | Uhlendorf et al. .............. 367/7 |
| 6,221,017 B1 | * | 4/2001 | Uhlendorf et al. ........... 600/443 |

\* cited by examiner

Primary Examiner—Marvin M. Lateef
Assistant Examiner—Ali M. Imam
(74) Attorney, Agent, or Firm—John Vodopia (57) ABSTRACT

A system and method for ultrasonic harmonic imaging of both tissue and tissue perfused with a contrast agent are disclosed. The ultrasonic harmonic imaging system comprises a wideband phased-array transducer, a transmitter for transmitting waves into the tissue, a receiver for receiving ultrasonic responses from the tissue, a control system electrically coupled to the transmitter and the receiver for controlling operation of the transmitter and receiver, a video processor, and a monitor. In a preferred embodiment, the transducer insonifies tissue at a fundamental frequency of less than approximately 1.5 MHz. A method for detecting an ultrasonic harmonic response of a contrast agent may be performed by introducing at least one contrast agent into the target object, destroying the contrast agent with an ultrasonic pressure wave and measuring the harmonic response from the destroyed contrast agent. A method for detecting an ultrasonic harmonic tissue response may be performed by insonifying the tissue at a low frequency for increased uniformity in depth and using transmit apodization of a wideband phased-array transducer to improve harmonic generation in the near-field.

62 Claims, 7 Drawing Sheets

WIDEBAND PHASED-ARRAY TRANSDUCER FOR UNIFORM HARMONIC IMAGING, CONTRAST AGENT DETECTION, AND DESTRUCTION

FIELD OF THE INVENTION

The present disclosure relates to ultrasonic imaging. More particularly, the invention relates to a system and method that permits uniform harmonic imaging and uniform contrast agent detection and destruction.

BACKGROUND OF THE INVENTION

Tissue Harmonic Background

Ultrasonic imaging has quickly replaced conventional X-rays in many clinical applications because of its image quality, safety, and low cost. Ultrasonic images are typically formed through the use of phased or linear array transducers which are capable of transmitting and receiving pressure waves directed into a medium such as the human body. Such transducers normally comprise multielement piezoelectric materials, which vibrate in response to an applied voltage to produce the desired pressure waves. Piezoelectric transducer elements are typically constructed of lead zirconate titanate (PZT), with a plurality of elements being arranged to form a transducer assembly. A new generation ultrasonic transducer known as a micro-machined ultrasonic transducer (MUT) is also available. MUTs are typically fabricated using semiconductor manufacturing techniques with a number of elements typically formed on a common substrate to form a transducer assembly. Regardless of the type of transducer element, the transducer elements may be further assembled into a housing possibly containing control electronics, the combination of which forms an ultrasonic probe. The ultrasonic probe may include acoustic matching layers between the surface of the various types of elements and the probe body. Ultrasonic probes may then be used along with an ultrasonic transceiver to transmit and receive ultrasonic pressure waves through the various tissues of the body. The various ultrasonic responses may be further processed by an ultrasonic imaging system to display the various structures and tissues of the body.

To obtain high quality images, the ultrasonic probe must be constructed so as to produce specified frequencies of pressure waves. Generally speaking, low frequency pressure waves provide deep penetration into the medium (e.g., the body), but produce poor resolution images due to the length of the transmitted wavelengths. On the other hand, high frequency pressure waves provide high resolution, but with poor penetration. Accordingly, the selection of a transmitting frequency has involved balancing resolution and penetration concerns. Unfortunately, resolution has suffered at the expense of deeper penetration and vice versa. Traditionally, the frequency selection problem has been addressed by selecting the highest imaging frequency (i.e., best resolution) which offers adequate penetration for a given application. For example, in adult cardiac imaging, frequencies in the 2 MHz to 3 MHz range are typically selected in order to penetrate the chest wall. Lower frequencies have not been used due to the lack of sufficient image resolution. Higher frequencies are often used for radiology and vascular applications where fine resolution is required to image small lesions and arteries affected by stenotic obstructions.

Recently, new methods have been studied in an effort to obtain both high resolution and deep penetration. One such method is known as harmonic imaging. Harmonic imaging is grounded on the phenomenon that objects, such as human tissues, develop and return their own non-fundamental frequencies, i.e., harmonics of the fundamental frequency. This phenomenon and increased image processing capabilities of digital technology, make it is possible to excite an object to be imaged by transmitting at a low (and therefore deeply penetrating) fundamental frequency ($f_o$) and receiving reflections at a higher frequency harmonic (e.g., $2f_o$) to form a high resolution image of an object. By way of example, a wave having a frequency less than 2 MHz can be transmitted into the human body and one or more harmonic waves having frequencies greater than 3 MHz can be received to form the image. By imaging in this manner, deep penetration can be achieved without a concomitant loss of image resolution.

Transducers have been designed for transmit frequencies in the range of 2 MHz to 3 MHz for sufficient resolution of cardiac valves, endocardial borders and other cardiac structures. Lower transmit frequencies have been used for Doppler but not for B-mode imaging. Heretofore, transmit frequency selection has been determined based on the capabilities of fundamental response imaging which required relatively high fundamental frequencies in order to obtain adequate resolution for diagnostic purposes.

However, in order to achieve the benefits of transmitting at a lower frequency for tissue penetration and receiving a harmonic frequency for improved imaging resolution, broadband transducers are required which can transmit sufficient bandwidth about the fundamental frequency and receive sufficient bandwidth about the harmonic(s). The s4 transducer available with the SONOS™ 5500 an ultrasound imaging system manufactured by and commercially available from Agilent Technologies, U.S.A., has a suitable bandwidth to achieve harmonic imaging with a single transducer thus providing a significant clinical improvement. Furthermore, the combination of the s4 transducer and the SONOS™ 5500 provide multiple imaging parameter choices using a single transducer, thus providing a penetration choice as well as a resolution choice.

However, several problems exist with the current harmonic imaging technology due to the fact that current transducer designs have been based on fundamental imaging and not harmonic imaging. The goal with harmonic imaging is to generate harmonic signals in the body of high enough intensity to be above the noise floor of the system. Theoretically, a harmonic signal will be more than 20 dB down from the fundamental backscatter and therefore wide dynamic range receivers are required. In the near-field, where harmonic responses have not yet formed and in the far-field where attenuation has taken over, it is not uncommon for a harmonic response to be 30–40 dB down from the fundamental backscatter. It is critical that the magnitude of the harmonic signal generated in the body be over both the noise floor of the system and the transmitted second harmonic backscatter. This is difficult to attain across the entire field of view, particularly in the near-field, where harmonics have not had the time to build and in the far-field where attenuation of the signal becomes a problem. In order to improve harmonic imaging the problem of non-uniform harmonic generation needs to be addressed.

Contrast Imaging Background

Harmonic imaging can also be particularly effective when used in conjunction with contrast agents. In contrast agent imaging, gas or fluid filled micro-sphere contrast agents known as microbubbles are typically injected into a medium, normally the bloodstream. Because of their strong nonlinear response characteristics when insonified at particular frequencies, contrast agent resonation can be easily detected by an ultrasound transducer. By using harmonic imaging after introducing contrast agents, medical personnel can significantly enhance imaging capability for diagnosing the health of blood-filled tissues and blood flow dynamics within a patient's circulatory system. For example, contrast agent harmonic imaging is especially effective in detecting myocardial boundaries, assessing microvascular blood flow, and detecting myocardial perfusion.

In addition to today's problems with Tissue Harmonic imaging, there are similar problems associated with the imaging of contrast agents. The power or mechanical index of the incident ultrasonic pressure wave directly affects the contrast agent acoustical response. At lower powers, microbubbles formed by encapsulating one or more gaseous contrast agents with a material forming a shell thereon resonate and emit harmonics of the transmitted frequency. The magnitude of these microbubble harmonics depends on the magnitude of the excitation signal pulse. At higher acoustical powers, microbubbles rupture and emit strong broadband signals. In order to take advantage of these strong backscattered signals for imaging purposes, it is desired to have uniform destruction within the imaging plane. In general, the higher the transmitted frequency, the greater the variation in the response from the microbubble within the imaging plane. It has been determined that lower frequencies are more efficient at bubble destruction than higher frequencies.

Today's systems, in order to deal with the lack of uniformity in bubble detection and bubble destruction, use multi-pulse techniques to increase the signal-to-noise ratio and to increase destruction of microbubbles. However, multi-pulse techniques for detection of contrast agents require the user to be able to discriminate motion artifacts from true bubble resonance and destruction signals. For example, in high mechanical index (MI) triggered techniques, such as Harmonic Power Doppler, it is critical that triggering occurs during that portion of the cardiac cycle when the heart is relatively stationary. Discriminating between motion artifacts resulting from triggering and variations in the cardiac cycle has made diagnosis difficult for users and has slowed acceptance of contrast imaging in clinical practices.

Several patents have been granted focusing on overcoming the signal-to-noise problem with harmonic imaging. U.S. Pat. No. 5,740,128 to Hossack et al. teaches a transmit element that minimizes the energy transmitted into the body at the range of frequencies where a response generated harmonic is expected as the transmitted energy can not be distinguished from a generated harmonic signal. The techniques revealed by Hossack address the dynamic range between the transmitted or fundamental frequency and the harmonic signal response. Hossack's techniques do not address non-uniform harmonic signal responses in near-field and far-field imaging planes.

U.S. Pat. No. 5,833,613 to Averkiou et al. teaches a multi-pulse transmission signal designed to minimize transmitted noise and to increase the harmonic signal. The technique transmits consecutive pulses with reversed polarities from one another into the body. Reflective addition of the pulses will subtract transmitted second harmonic reflections (undesired) and will cause the generated harmonic waveforms, which return to the transducer in phase, to add coherently thus increasing the signal-to-noise ratio. Like U.S. Pat. No. 5,740,128 to Hossack et al., Averkiou's multi-pulse technique does not address non-uniform harmonic signal responses. Averkiou's multi-pulse technique is susceptible to motion artifacts generated by each subsequent return of the multiple transmission pulses. In addition, Averkiou's multi-pulse technique increases signal-processing overhead, which leads to a decrease in frame rate for real-time ultrasound diagnostic systems.

A second U.S. Pat. No. 5,879,303, to Averkiou et al., teaches a method for ultrasonic imaging using reflections from both the fundamental and one or more harmonic signals in the presence of depth dependent ultrasound signal attenuation. The '303 patent to Averkiou further teaches that by removing reflections from the fundamental and using only generated harmonics to create the image, multi-path clutter from undesired structures in the near-field may be removed. While the '303 patent discusses a need to reduce multi-path clutter in the near-field, the '303 patent fails to address the need to quickly generate harmonic signal responses in the near-field, where the generated harmonic signals are generally 30 dB down from the fundamental. In addition, the '303 patent fails to address the need for deeper signal penetration in order to generate harmonic signal responses with a suitable energy level in the far-field where the energy is also more than 30 dB down.

U.S. Pat. No. 5,558,092 to Unger et al. discloses methods and apparatus for performing diagnostic and therapeutic ultrasound simultaneously. Unger introduces a specialized transducer with "diagnostic" elements and "therapeutic" elements. The therapeutic elements are intended to rupture vesicles (microbubbles) containing drugs/genes or other therapeutic materials, while the diagnostic elements are available to monitor results of the rupture events. Unger teaches low frequency high power ultrasonic signals to enhance rupturing of the vesicles for therapeutic reasons. Unger's transducers are complicated, difficult to manufacture, and expensive. The transducers also suffer in performance from a typical phased-array transducer because the full aperature can not be used for imaging as a significant portion of the transducer is dedicated to therapeutic insonification.

U.S. Pat. No. 5,410,516 to Uhlendorf et al. discloses contrast agent imaging along with single pulse excitation techniques such as harmonic imaging. Specifically, Uhlendorf teaches that by choosing a radio-frequency (RF) filter to selectively observe any integer harmonic (2nd, 3rd, etc.), subharmonic (e.g., 1/2 harmonic) or ultraharmonic (e.g., 3/2 harmonic) it is possible to improve the microbubble to tissue ratio. The second harmonic has proven most useful due to the large bubble response at this frequency as compared to higher order integer harmonics, subharmonics or ultraharmonics. The second harmonic also is most practical due to bandwidth limitations on the transducer (i.e., <70% bandwidth, where percent bandwidth is defined as the difference of the high corner frequency −6 dB point from the low corner frequency −6 dB point, divided by the center frequency. However, single pulse excitation techniques together with harmonic imaging suffer from poor microbubble-to-tissue ratio as large tissue integer-harmonic signals mask the signal generated by the contrast agent.

SUMMARY OF THE INVENTION

In response to these and other shortcomings of the prior art the present invention relates to an improved ultrasonic imaging system for harmonic imaging of an object in a medium. Briefly described, in architecture, the system can be implemented with a wideband phased-array transducer, a transmitter which generates electrical signals that may be converted by the transducer to fundamental ultrasonic pressure waves for transmission into a medium, a receiver for receiving harmonic ultrasonic responses from at least one object in the medium, and a control system electrically coupled to the transmitter and the receiver for controlling operation of the transmitter and the receiver.

The present invention can also be viewed as providing a method for uniform harmonic imaging, contrast agent detection and destruction. In this regard, the method can be broadly summarized by the following steps: introducing at least one contrast agent; insonifying tissue with an ultrasound signal at a fundamental frequency less than 1.5 MHz of a sufficient magnitude such that homogenous contrast agent destruction occurs within a single pulse; receiving echoes at one or more harmonic frequencies of the fundamental frequency, filtering out harmonic responses from tissue and processing the echoes to produce an image of the object.

The present invention can also be viewed as providing a method for uniform harmonic imaging without a contrast agent. In this regard, the method can be broadly summarized by the following steps: insonifying tissue with an ultrasound signal at a fundamental frequency less than or equal to 1.5 MHz; using transmit apodization to generate tissue generated harmonic responses in the near-field; receiving echoes at one or more harmonic frequencies of the fundamental frequency; and processing the echoes to produce an image of the object.

An ultrasonic imaging system in accordance with the present invention is designed to increase harmonic generation responses in the article under observation at the expense of resolution, by creating a more uniform transmit power field throughout the entire image. Uniformity in the transmit power field due to the lower transmit frequency provides for improved tissue harmonic response imaging. After introducing one or more contrast agents into the tissue of interest, a more uniform power field provides homogeneous contrast agent microbubble destruction. In addition, a more uniform power field provides for homogeneous microbubble detection after the tissue harmonics have been filtered from the response.

The improved ultrasonic imaging system in accordance with the present invention uses a wideband (>70%, 6 dB, 2-way bandwidth) phased-array transducer technology for uniform harmonic generation and uniform microbubble detection and destruction at transmit frequencies less than 1.5 MHz. The ultrasonic imaging system displays a tissue generated harmonic response signal, which is above the noise floor of the system throughout the image—not just in the mid-field. The increased signal to noise ratio throughout the image results in an image of improved quality.

In addition to improved imaging quality for insonified tissue, ultrasonic pressure wave uniformity creates a more uniform microbubble response in the ultrasound field allowing different regions to be compared in terms of concentration of the contrast agent. In turn, regional comparisons of contrast agent concentration will allow regional comparisons of perfusion, thereby permitting improved imaging of blood flow throughout the circulatory system of a patient. By using a lower fundamental frequency pressure wave transmission (e.g., <1.5 MHz), it becomes possible to destroy contrast agents uniformly with a single transmit pulse. This is due to the more uniform power field present that results from the lower fundamental frequency and from the fact that low frequencies more efficiently destroy some contrast agents. When a rapid destruction of contrast agent occurs, a broadband response is back scattered from the destroyed microbubbles. This broadband contrast response, although somewhat detectable at higher frequencies, has an increased magnitude at lower frequencies (higher signal to noise). Furthermore, newer designs of broadband transducers (e.g., >70%) make it possible to receive and process ultrasonic responses between the 2nd and 3rd harmonics where responses from tissue are minimal and a relatively stronger microbubble response signal is present. Improved electromechanical properties have been observed with single crystals of $Pb(Zn_{1/3}Nb_{2/3}O_3$—$PbTiO_3)$ (PZN-PT) and $Pb(Mg_{1/3}Nb_{2/3})O_3$—$PbTiO_3$ (PMN-PT). Using these materials, longitudinal coupling constants, $k_{33}$, of 85% to 93% have been observed as compared with conventional PZT-type ceramics, which normally exhibit a $k_{33}$ value of approximately 70% to 75%. As known in the art, the coupling constant, $k_{33}$, represents the efficiency of conversion of electrical energy to mechanical energy and vice versa. This high coupling of PZN-PT and PMN-PT single crystals provides the potential for improved sensitivity and bandwidth in transducer design.

Other systems, methods, features, and advantages of the present invention will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims.

Figure 1:
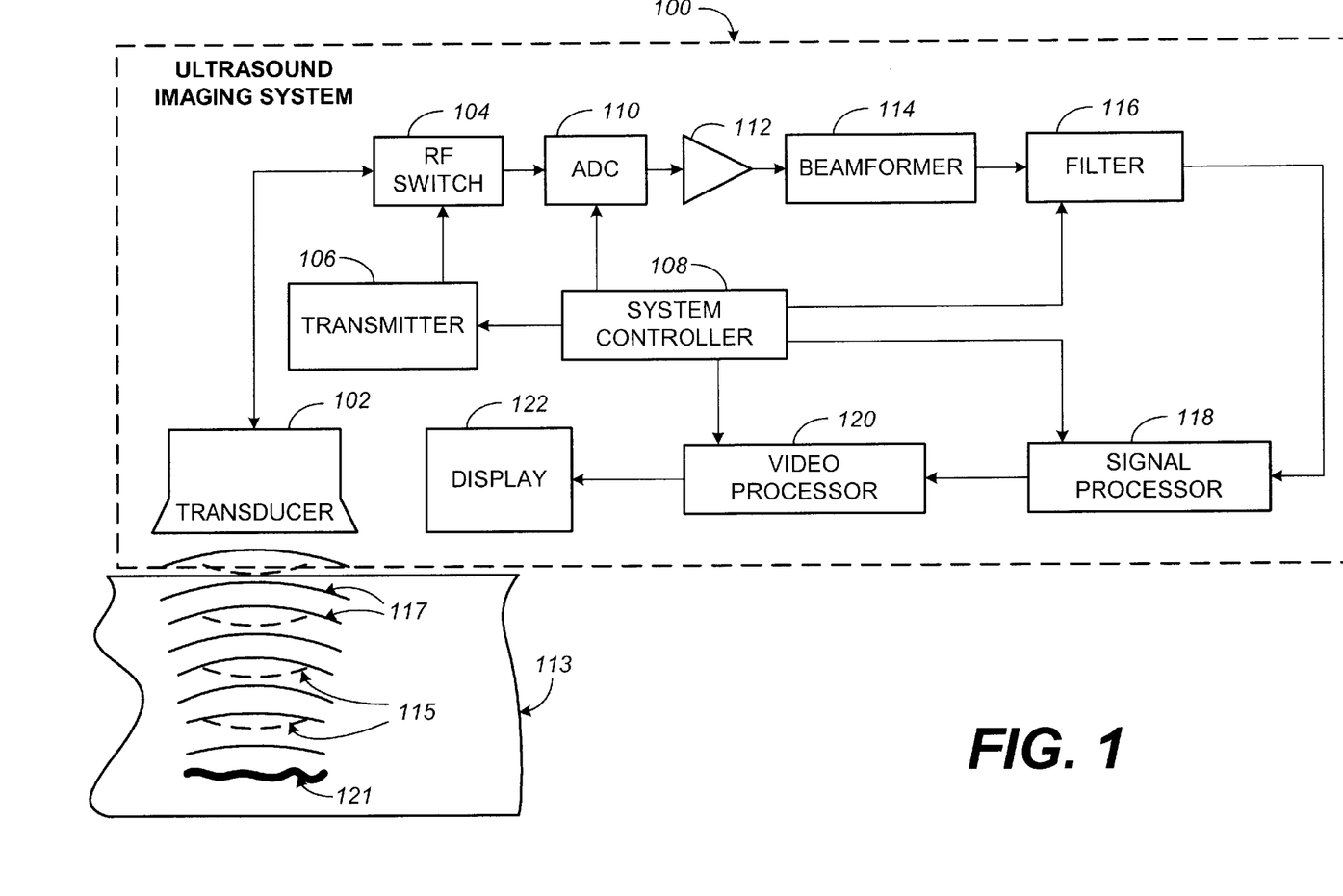
FIG. 1 is a block diagram of an ultrasonic imaging system consistent with the teachings of the present invention.

Turning now to the drawings, wherein like referenced numerals designate corresponding parts throughout the drawings, reference is made to FIG. 1, which illustrates a block diagram of an ultrasound imaging system capable of viewing tissue and contrast agent(s).

In this regard, an ultrasound imaging system 100 may comprise a transducer 102, a RF switch 104, a transmitter 106, a system controller 108, an analog to digital converter (ADC) 110, a time gain control amplifier 112, a beamformer 114, a filter 116, a signal processor 118, a video processor 120, and a display 122. The transducer 102 may be electrically coupled to RF switch 104. The RF switch 104 may be configured as shown with a transmit input coupled from the transmitter 106 and a transducer port electrically coupled to the transducer 102. The output of RF switch 104 may be electrically coupled to an ADC 110 before further processing by the time gain control amplifier 112. The time gain control amplifier 112 may be coupled to a beamformer 114. The beamformer 114 may be coupled to the filter 116. The filter 116 may be further coupled to a signal processor 118 before further processing in the video processor 120. The video processor 120 may then be configured to supply an input signal to a display 122. The system controller 108 may be coupled to the transmitter 106, the ADC 110, the filter 116, and both the signal processor 118 and the video processor 120 to provide necessary timing signals to each of the various devices.

As will be appreciated by persons having ordinary skill in the art, the system controller 108 can include one or more processors, computers, and other hardware and software components for coordinating the overall operation of the ultrasonic imaging system 100. In addition, it will be appreciated that the system controller 108 may include software which comprises an ordered listing of executable instructions for implementing logical functions, which can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. The computer readable medium can be, for instance, an electronic, magnetic, optical, electromagnetic, infrared, or semiconductor system, apparatus, device, or propagation medium.

The RF switch 104 isolates the transmitter 106 of the ultrasound imaging system 100 from the ultrasonic response receiving and processing sections comprising the remaining elements illustrated in FIG. 1. The system architecture illustrated in FIG. 1 provides an electronic transmit signal generated within the transmitter 106 that is converted to one or more ultrasonic pressure waves herein illustrated by ultrasound lines 115. When the ultrasound lines 115 encounter a tissue layer 113 that is receptive to ultrasound insonification the multiple transmit events or ultrasound lines 115 penetrate the tissue 113. As long as the magnitude of the multiple ultrasound lines 115 exceeds the attenuation affects of the tissue 113, the multiple ultrasound lines 115 will reach an internal target 121. Those skilled in the art will appreciate that tissue boundaries or intersections between tissues with different ultrasonic impedances will develop ultrasonic responses at harmonics of the fundamental frequency of the multiple ultrasound lines 115.

As further illustrated in FIG. 1, such harmonic responses may be depicted by ultrasonic reflections 117. It will be further appreciated that tissue insonified with ultrasonic waves develops harmonic responses because the compressional portion of the insonified waveforms travels faster than the rarefactional portions. The different rates of travel of the compressional and the rarefactional portions of the waveforms causes the wave to distort producing an harmonic signal which is reflected or scattered back through the various tissue boundaries. It is significant to note that while FIG. 1 illustrates only a second harmonic response to the incident multiple ultrasound lines 115 impinging the internal target 121 within the tissue layer 113, other harmonic responses may also observed. As by way of example, it is known that subharmonic, harmonic, and ultraharmonic responses may be created at the tissue boundary between tissue layer 113 and the internal target 121. The internal target 121 alone will produce harmonic responses at integer multiples of the fundamental frequency. Various contrast agents on the other hand, have been shown to produce subharmonic, harmonic, and ultraharmonic responses. Hereinafter, subharmonic and ultraharmonic responses may be designated as non-integer harmonic responses.

Those ultrasonic reflections 117 of a magnitude that exceeds the attenuation effects from traversing tissue layer 113 may be monitored and converted into an electrical signal by the combination of the RF switch 104 and transducer 102. The electrical representation of the ultrasonic reflections 117 may be received at the ADC 110 where they are converted into a digital signal. The time gain control amplifier 112 coupled to the output of the ADC 110 may be configured to adjust amplification in relation to the total time a particular ultrasound line 115 needed to traverse the tissue layer 113. In this way, response signals from one or more internal targets 121 will be gain corrected so that ultrasonic reflections 117 generated from relatively shallow objects do not overwhelm in magnitude ultrasonic reflections 117 generated from insonified objects further removed from the transducer 102.

The output of the time gain control amplifier 112 may be beamformed, filtered and demodulated via beamformer 114, filter 116, and signal processor 118. The processed response signal may then be forwarded to the video processor 120. The video version of the response signal may then be forwarded to display 122 where the response signal image may be viewed. It will be further appreciated by those of ordinary skill in the art that the ultrasonic imaging system 100 may be configured to produce one or more images and or oscilloscopic traces along with other tabulated and or calculated information that would be useful to the operator.

Wideband Phased-Array Transducer

To achieve desired uniform harmonic generation and uniform microbubble detection and destruction at transmit frequencies less than 1.5 MHz, the ultrasonic imaging system 100 uses a wideband (>70%, 6 dB, 2-way bandwidth) phased-array transducer 102. The ultrasonic imaging system 100 creates one or more pressure waves that generate a tissue generated harmonic response signal, which is above the noise floor of the system throughout the image—not just in the mid-field. The increased signal to noise ratio throughout the image results in an image of improved quality.

In addition to improved imaging quality for insonified tissue, ultrasonic pressure wave uniformity creates a more uniform microbubble response in the ultrasound field allowing different regions to be compared in terms of concentration of the contrast agent. In turn, regional comparisons of contrast agent concentration will allow regional comparisons of perfusion, thereby permitting improved imaging of blood flow throughout the circulatory system of a patient. By using a lower fundamental frequency pressure wave transmission (e.g., <1.5 MHz), it becomes possible to destroy contrast agents uniformly with a single transmit pulse. This is due to the more uniform power field present that results from the lower fundamental frequency and from the fact that low frequencies more efficiently destroy some contrast agents.

In a preferred embodiment, the wideband phased-array transducer 102 utilizes single crystals composed of PMN-PT and/or PZN-PT. For the purposes of the present invention, the term single crystal is used to denote oriented polycrystals, in which the crystal comprises very few grains (all aligned in the same direction), and single grain crystals, in which the crystal comprises only a single grain of material. To fabricate these elements, chemical grade PbO, MgO, ZnO, $Nb_2O_5$, and $TiO_2$ may be used to form PMN-PT and PZN-PT compositions. Once the compositions were formed, PMN-PT and PZN-PT single crystals may be grown using the Bridgman and flux technique, and may be oriented via the Laue back reflection method. Next, the crystals may be sliced using an inter-dimensional (ID) saw parallel to the (001), (011), and (111) planes to approximately 1 mm in thickness.

From Table I, it can be appreciated that several different thickness/width cut orientations can be beneficially used in creating a wideband transducer. Due to the particularly desirable properties obtained from single crystal wafers having <001> and <011> thickness orientations, these wafers represent the preferred orientations for crystals that may be used in constructing transducers. Once sliced, the wafers may then be lapped and polished. Gold coating may be applied to both surfaces of the wafers to form electrodes. The single crystal wafers may then be diced on a dicing saw into thin slivers with various width orientation cuts. The slivers may then be poled and measured at room temperature.

After completing transducer material fabrication, the electromechanical properties of the various single crystal slivers may be evaluated. Table I lists the piezoelectric and dielectric properties for various slivers. As shown in the table, very high effective coupling constants, may be obtained for slivers ($k_{33}'$=84% to 90%) constructed in accordance with above description.

TABLE I

Effective Coupling Constants and Dielectric Constants of PMN-PT and PZN-PT Slivers

| | Effective Coupling Constant ($k_{33}'$) | Clamped Dielectric Constant (K) |
|---|---|---|
| PMN-PT 30–32% (rhombohedral) | | |
| $<001>_t/<010>_w$ | 0.86–0.89 | 1400 |
| $<011>_t/<211>_w$ | 0.90 | 1100 |
| $<011>_t/<522>_w$ | 0.90 | 1100 |
| $<011>_t/<311>_w$ | 0.90 | 1100 |
| $<011>_t/<110>_w$ 35 degrees | 0.72 | 1100 |
| PZN-PT 4.5% PT (rhombohedral) | | |
| $<001>_t/<010>_w$ | 0.84–0.87 | 1100 |
| PZN-PT 8% PT (rhombohedral) | | |
| $<001>_t/<010>_w$ | 0.85–0.88 | 900 |

For one-dimensional (ID) transducer applications, the single crystal elements may be diced into one-dimensional or quasi-one dimensional sliver shapes where the length>height>width. Not only the thickness orientations, but also the width orientations, affect the electromechanical properties of the slivers. As illustrated in Table I, the effective coupling constant ($k_{33}'$ for slivers) replaces the longitudinal coupling constant ($k_{33}$ for bars) due to the clamping effect from the length dimension of the sliver. By effectively selecting the thickness and width orientations, very high $k_{33}'$ (from 0.70 to 0.90) for sliver samples can be obtained, which is very close to the $k_{33}$ value of bar samples.

Utilizing the large coupling constant, $k_{33}$, obtainable with such single crystals of PMN-PT and PZN-PT, in conjunction with additional improvements such as multiple matching layers, voltage biasing, and multiple-layer design, described hereinafter, single crystal transducers can be designed with extremely wide bandwidth. In particular, the additional bandwidth achieved through the use of single crystal transducers, higher harmonic frequencies, even those beyond the second harmonic, can be imaged. In addition, such a single crystal transducer with more than 100% bandwidth can offer a wide range of second harmonic frequency choices. As will be understood by persons having ordinary skill in the art, this additional bandwidth creates several application possibilities which either were not possible with conventional transducers, or which were not nearly as useful due to the limitations of such transducers.

One disadvantage related to the use of PMN-PT and PZN-PT single crystals in manufacturing ultrasonic transducers concerns difficulty associated with acoustic matching. The problem of acoustic matching can, however, be overcome through the use of matching layers. In particular, the utilization of multiple matching layers can effectively couple the acoustic energy from the transducer into the body, therefore improving the bandwidth significantly.

Figure 2:
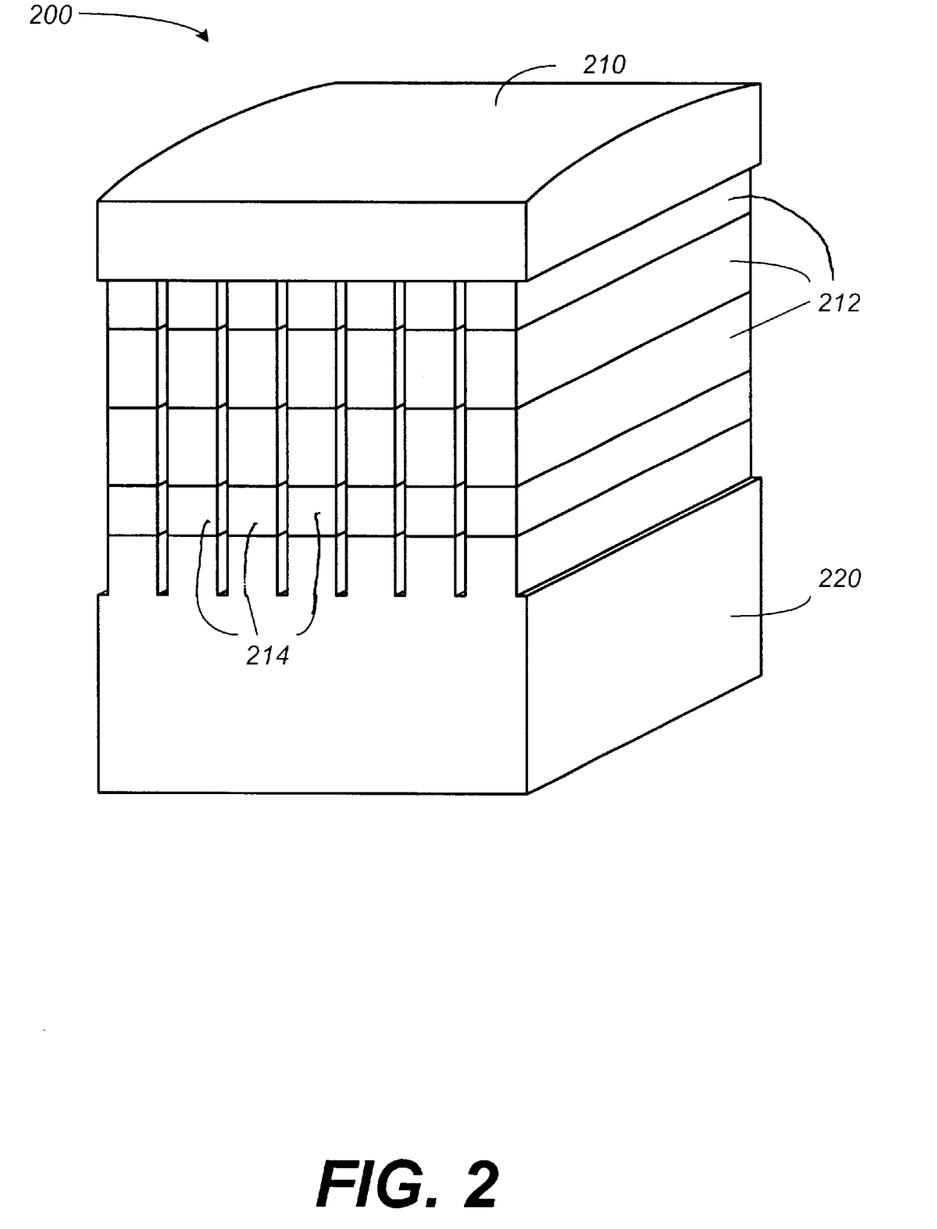
FIG. 2 is a perspective drawing of an ultrasonic transducer having single crystal element slivers and multiple matching layers that can be integrated with the ultrasonic imaging system of FIG. 1.

In this regard, FIG. 2 illustrates an ultrasonic transducer 200 comprising single crystal element slivers 214 which also includes multiple matching layers. As shown in FIG. 2, the ultrasonic transducer 200 comprises a backing 220 and an acoustic lens 210. Interposed between the slivers 214 and the acoustic lens 210 are, in this example, three matching layers 212. As is discussed hereinafter, the use of three such matching layers 212 in combination with single crystal slivers 214 render unexpectedly advantageous results in terms of ultrasonic transducer 200 properties.

Figure 3A:
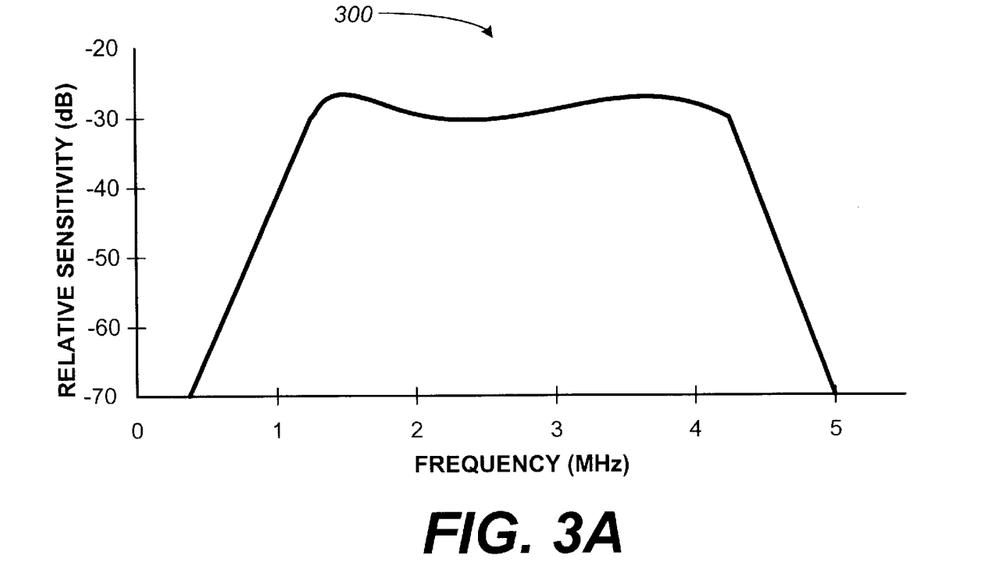
FIG. 3A is a modeled frequency response of the wideband single crystal ultrasonic transducer of FIG. 2.

Table II illustrates modeled bandwidth data of PMN-PT single crystal transducers ($<001>_t/<010>_w$ or $<011>_t/<110>_{w\ 50-75\ degree}$ cuts) with various members of matching layers. As shown in Table II, approximately 105% of −6 dB bandwidth was determined to be possible in using three matching layers. FIG. 3A illustrates a modeled frequency response 300 for ultrasonic signals transmitted and received via the modeled transducer.

TABLE II

Statistic Bandwidth Data of Modeled PMN-PT Single Crystal Transducers with Multiple Acoustic Matching Layers

| Bandwidth | (−6 dB) | (−20 dB) | (−40 dB) |
|---|---|---|---|
| 2 Layer Design: | 95% | 120% | 160% |
| 3 Layer Design: | 105% | 130% | 160% |
| 4 Layer Design: | 113% | 135% | 165% |

Figure 3B:
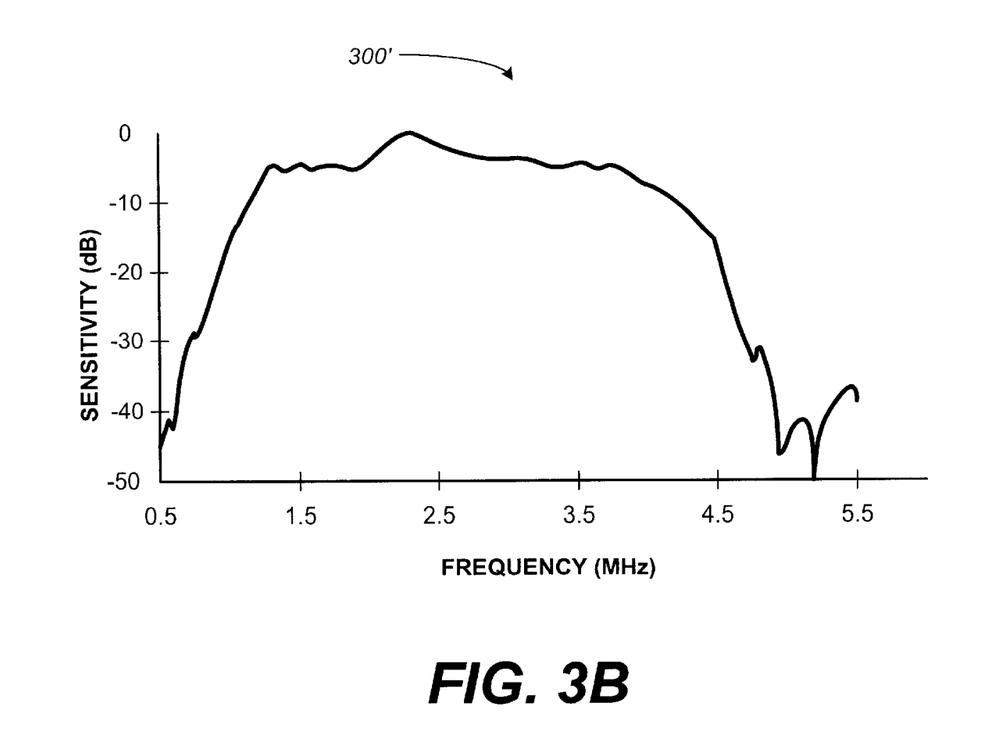
FIG. 3B is an actual response of an experimental version of the wideband single crystal ultrasonic transducer of FIGS. 1 and 2.

A wideband phased-array transducer 102 using a PMN-PT single crystal may be constructed which closely matches the model of FIG. 3A. The actual frequency response 300' of a phased-array transducer 102 with a center frequency of 2.7 MHz is illustrated in FIG. 3B. The phased-array transducer 102 used to create the frequency response 300' had 80 active elements with an element pitch of 254 μm. A single layer of PMN-PT single crystal ($<001>_t/<010>_w$, and $<011>_t/<110>_{w50-75\ degree}$ cuts) was used as the piezoelectric layer in conjunction with three matching layers to improve acoustic impedance matching. A room-temperature vulcanized (RTV) acoustic lens was added in front of the matching layers to obtain the acoustic focus. The transducer was integrated to an ultrasound imaging system 100 via a series inductor and a cable 6 feet in length.

The PMN-31% PT with sliver orientation of $<001>_c$/$<010>_w$ was used to build the transducer. The effective coupling constant ($k_{33}'$) of the sliver was 0.88 and clamping dielectric constant, K, was 1,200. The PMN-PT single crystal plate (<001> orientation) and matching layers were bonded together with epoxy and diced into a one-dimensional array. The thickness to width aspect ratio (t/w) of the sliver was about 0.5. More than 99% of the elements survived the transducer build. In the experiment, the center frequency was at 2.7 MHz with −6 dB band edges of 1.15 MHz at the low frequency side (low corner frequency) and 4.1 MHz at the high frequency side (high corner frequency). As a result, the total −6 dB bandwidth for the transducer may be calculated as shown below.

$$\% \ BW = 100 * \left( \frac{(UpperCorner_f - LowerCorner_f)}{Center_f} \right) \quad \text{(Eq. 1)}$$

$$\% \ BW = 100 * ((4.1 - 1.15)/2.7) = 109\%$$

The −20 dB bandwidth was 130% for this transducer. The above data indicates that a very wide bandwidth (more than 100% of −6 dB bandwidth) may be obtained in single crystal transducers with optimized electrical and acoustic design. The extra bandwidth achieved from multiple matching layer single crystal transducers, such as that exemplified by the frequency response 300' illustrated in FIG. 3B, can offer a wider range of second harmonic frequency choices. For example, transmitted fundamental frequencies can be selected at 1.2, 1.5, 1.8, and 2.0 MHz, and the received second harmonic frequencies may be selected at 2.4, 3.0, 3.6, and 4.0 MHz.

In addition to acoustic matching, another concern regarding use of PMN-PT and PZN-PT materials is that the piezoelectric and dielectric properties of PMN-PT and PZN-PT single crystal materials are not stable near the morphotropic phase boundary (MPB) due to the phase transition from rhombohedral to tetragonal phases PMN-PT crystals grown by the Bridgman technique have shown a compositional fluctuation along the growing axis with Ti content continuously drifting along the growing direction. This characteristic makes these crystals more difficult for compositions near the MPB regions. Away from the MPB, the piezoelectric and dielectric constants of rhombohedral phase crystals are more uniform. However, these compositions have an even lower Curie temperature compared to the typical PZT-type ceramics used for medical imaging applications, and therefore are more susceptible to depoling during the fabrication, and device storage/operating temperature changes.

Figure 4:
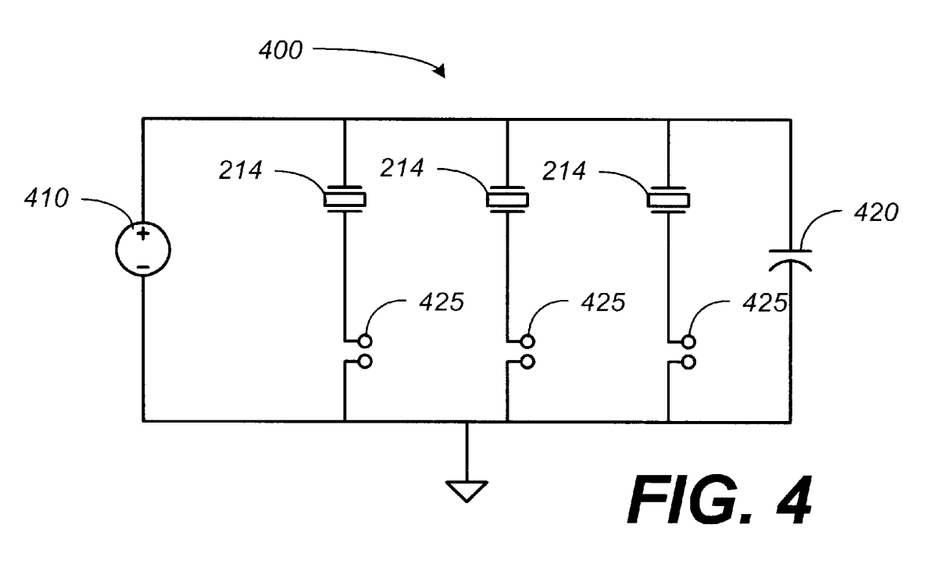
FIG. 4 is a circuit schematic illustrating voltage biasing of the single crystal transducer of FIG. 2.

To improve temperature stability of single crystal transducers, it has been determined that a voltage bias (e.g., DC bias) may be applied to the transducer 102 to maintain the polarization of the transducer 102 during operation. Under this voltage bias, the piezoelectric element material is highly polarizable and maintains its piezoelectric properties. Because the dielectric and piezoelectric properties of single crystals with low PT content depend upon the magnitude of the DC voltage bias applied, the pulse-echo response of a transducer element can be at least partially controlled by varying the magnitude of the DC voltage bias. In this regard, FIG. 4 is an electrical schematic 400 that illustrates application of a voltage bias to a plurality of piezoelectric element slivers 214. As indicated in the figure, the DC voltage bias is applied to the slivers 214 with a voltage source 410 electrically coupled to each of the slivers 214 in parallel. Also connected in the circuit is a bypass capacitor 420, which allows the transmitted signal to drain (i.e., go to ground). In addition, a transmit and receive connection 425 may be provided in series with each of the slivers 214.

By utilizing a DC bias, the designer can add one more degree of freedom in the development of the transducers. For PMN-PT and PZN-PT systems, this allows the transducer to be operated under an extremely wide composition range, even those in which depoling would occur if bias were not applied to the crystal. Since the bias voltage can stabilize the polarization, the PMN-PT and PZN-PT single crystals can be used in devices with very low phase-transition temperatures from rhombohedral to cubic and also from rhombohedral to tetragonal. By way of example, from approximately 10% to 40% by composition of PT in PMN-PT systems, and from approximately 3% to 12% by composition of PT in PZN-PT systems are possible.

In some instances, a constant application of bias may not be necessary. Accordingly, the polarization of the single crystal transducers can be refreshed during each regular operation. In addition, a poling voltage can also be added periodically to the single crystal layer(s) to maintain the bandwidth and sensitivity of the transducer. Furthermore, the poling voltage can be added during the operations or between the mode switching from two-dimensional imaging to Doppler, or from Doppler to Color Flow, and the like. In such cases, a constant DC voltage bias is not required during regular ultrasonic transducer operation.

Figure 5A:
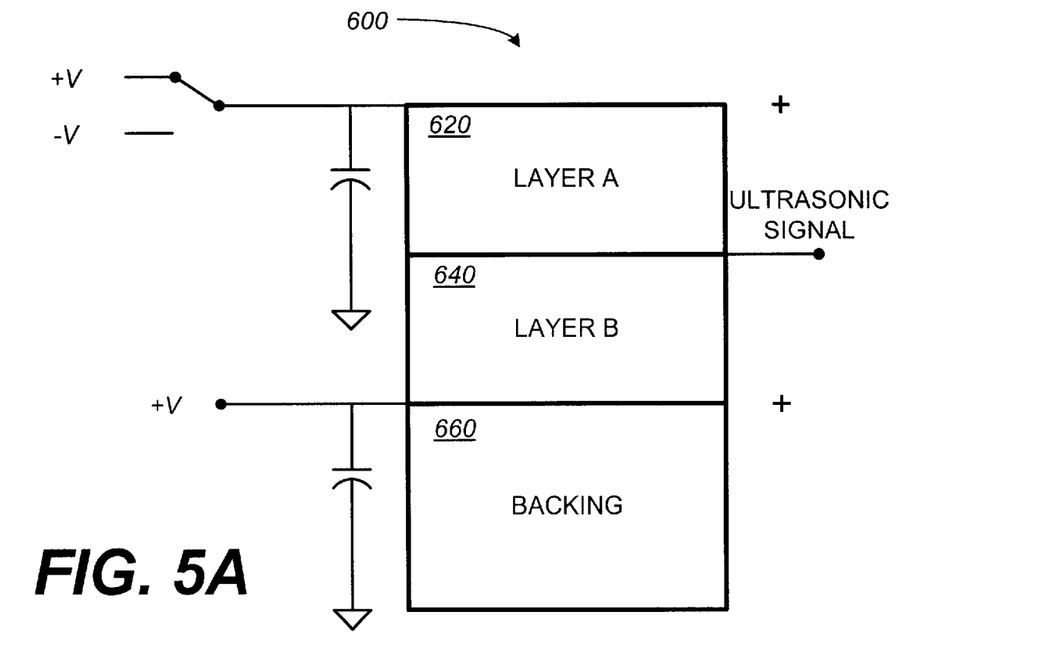
FIGS. 5A and 5B are schematic illustrations of polarity biasing multi-layered single crystal transducer elements to produce enhanced bandwidth characteristics.
Figure 5B:
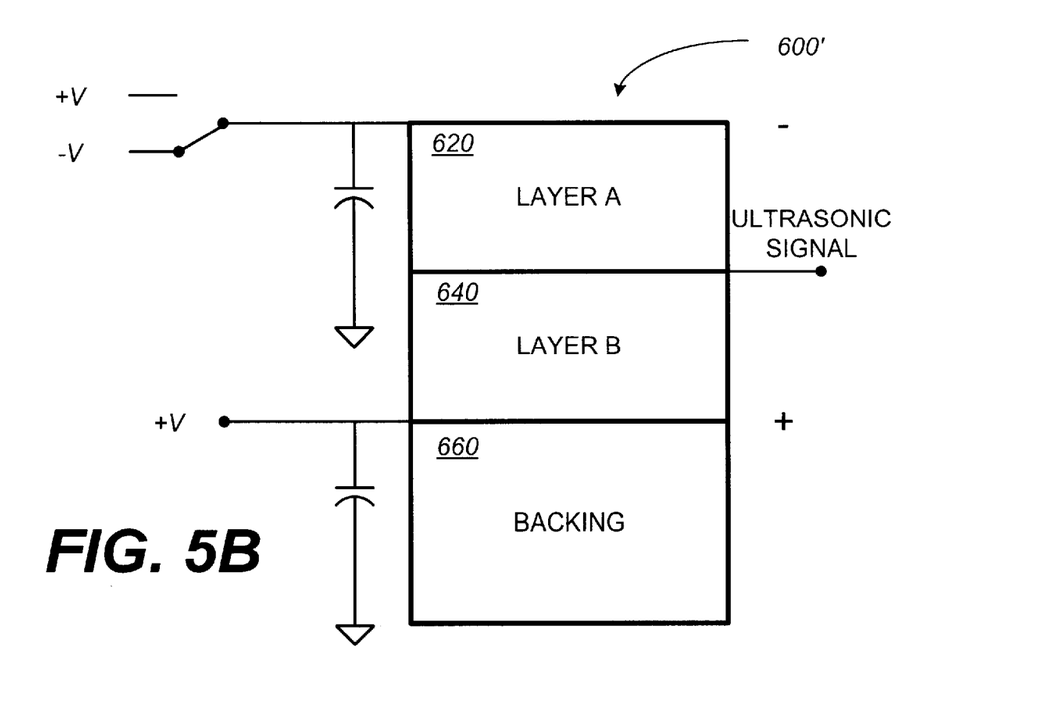

In addition to the use of matching layers and voltage biasing, advantageous results can also be obtained with multiple single crystals. FIGS. 5A and 5B illustrate an exemplary multiple layer single crystal transducer 600, 600', respectively. As shown in these figures, the single crystal transducer 600, 600' may comprise a stack of two layers herein designated layer A 620 and layer B 640. Each of the single crystal layers A, B 620, 640 of either PMN-PT or PZN-PT may be connected electrically in parallel. Although two such layers are shown for the purposes of example, it is to be understood that more than two layers could be used, if desired. A backing 660 may also be provided. An ultrasonic signal may be provided between layer A 620 and layer B 640 as is further illustrated in the schematics of FIGS. 5A and 5B. The polarization of each single crystal layer 620, 640 can be selected independently with a DC voltage bias of a particular polarity. When layers 620, 640 are acoustically poled in series or in parallel, the stack can be excited to produce two different resonant frequencies. In the first case, as shown in FIG. 5A, the layers 620, 640 are acoustically in series, although they have polarizations that directly oppose each other (either through initial poling or the application of a voltage bias). When an excitation pulse is applied to the pair, the structure resonates in the same manner as a single layer whose thickness is the sum of the thickness of the double layers. The resonant frequency of the stack may be determined as shown below.

$$f_1 = v/4t = f_o \quad \text{(Eq. 2)}$$

where, v is the sound velocity of the single crystal and t is the thickness of each layer. As a result, the arrangement shown in FIG. 5A is particularly useful in obtaining lower frequencies.

In the second case, depicted in FIG. 5B, the electric fields and polarization in each of the layers A,B 620, 640 are in the same direction. Because of this arrangement, when an electric field is applied to the central electrode, the structure resonates in the same manner as a single layer whose thickness is equal to the thickness of each individual layer. The resonant frequency of the stack may be determined as shown below.

$$f_2 = v/2t = 2*f_o \qquad \text{(Eq. 3)}$$

From this, it can be appreciated that the arrangement shown in FIG. 5B is particularly useful to produce higher frequencies.

Another advantage of double or multi-layer designs is that the electrical impedance of the transducer can be dramatically reduced to more closely match the transducer with the medium being examined. The small element size and high electrical impedance of single layer transducer arrays may hurt the signal to noise ratio for a wideband design. In the case of a multi-layer array comprising N layers of single crystals electrically connected in parallel, the capacitance of each element is increased by a factor of N. In addition, when the layers are acoustically in series (as shown in FIG. 5A), the total thickness of the stack is divided by the number of layers and thereby increases the capacitance by another factor of N. This high capacitance allows the transmitter to communicate with the transducer elements more efficiently, therefore improving the signal to noise ratio and increasing the bandwidth.

Figure 6:
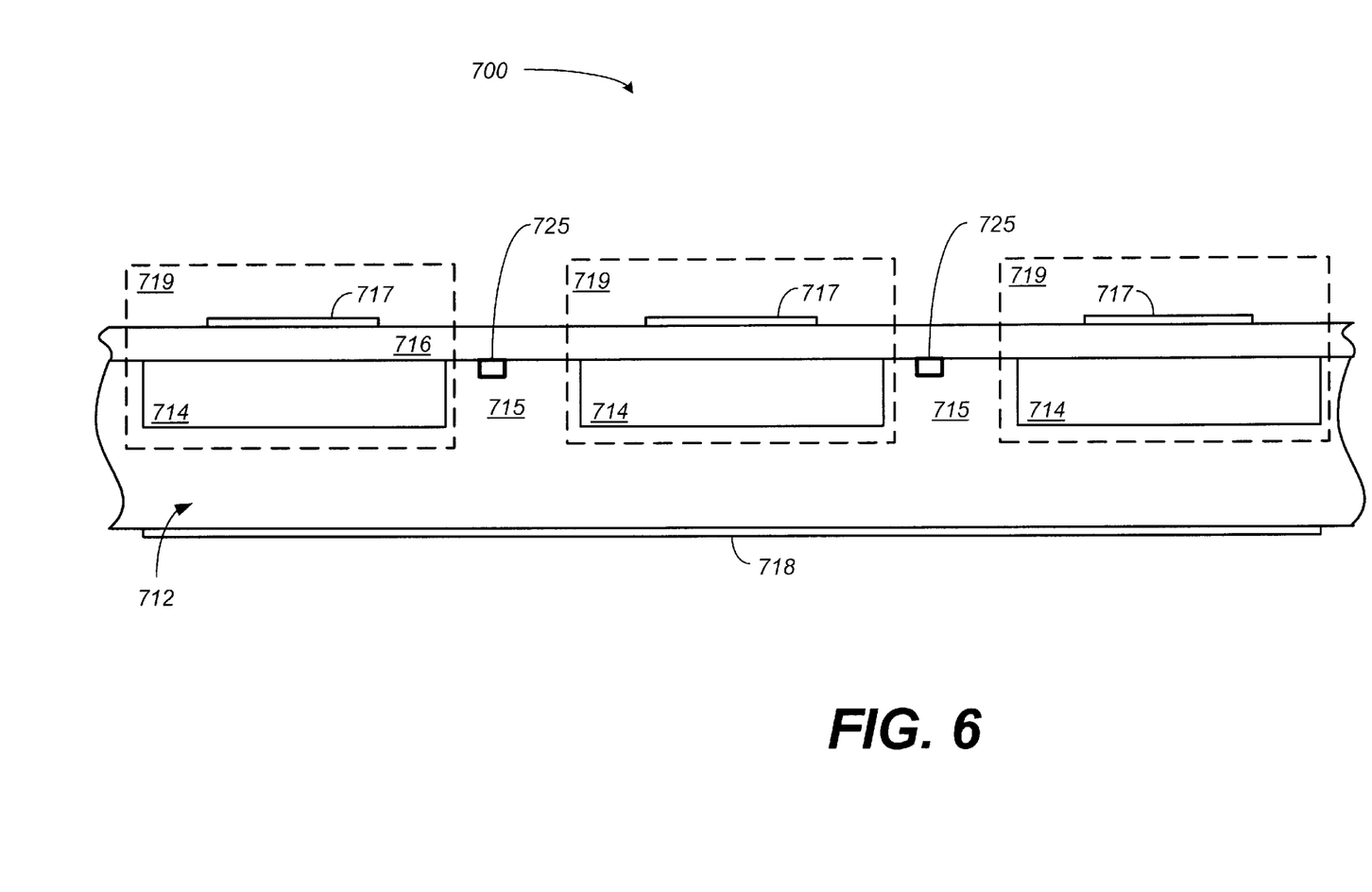
FIG. 6 is a simplified cross-sectional view illustrating a micro-machined ultrasonic transducer (MUT) that can be integrated with the ultrasonic imaging system of FIG. 1.

It is important to note that the response characteristics associated heretofore with a multi-element single crystal transducer may be accomplished with a MUT. In this regard, FIG. 6 illustrates a MUT 700 in accordance with the present invention. As illustrated MUT 700 may comprise a plurality of MUT cells 719 formed over a substrate 712, which may be a semiconductor material such as silicon and which may also form support elements 715 for a MUT membrane 716. Alternatively, the support elements 715 may be constructed of another material grown or applied to the substrate 712. The MUT membrane 716, the support elements 715, and the substrate 712 define a gap 714, which may be exposed to ambient pressure or which may contain a vacuum, depending upon the desired application. A first electrode 718 may be applied to one surface of the substrate 712 and a second electrode 717 may be applied to the membrane 716 as shown. When the MUT cell 719 is used in a transmit mode, membrane 716 oscillates when excited by a voltage signal applied between the first and second electrodes 718, 717, thus producing an ultrasonic pressure wave. When MUT cell 719 is used in a receive mode, acoustic pressure in the form of ultrasonic reflections 117 (see FIG. 1) generated from an object impinges upon the membrane 716 causing the membrane 716 to oscillate. Each of the plurality of MUT cells 719 may be polled for an electrical equivalent of the incident ultrasonic reflections at each of the respective MUT cells 719.

One or more control apparatus 725 (two shown) may also be included with MUT 700. The one or more control apparatus 700 may provide aperture and apodization control to the plurality of MUT cells 719. Typically, one control apparatus is provided with each MUT 700. However, MUT cells 719 may be each associated with a control apparatus 725.

The control apparatus 725 may take the form of switches, such as field effect transistors, formed on the substrate 712 or may be implemented via other various switching techniques, such as, but not limited to, micro-machined relays. The control apparatus 725 may also take the form of a bias voltage used to excite MUT 700 in a manner that provides control over the aperture, elevation, and apodization of the MUT 700.

Harmonic Applications

Because of the beneficial properties of PMN-PT and PZN-PT materials, transducer elements comprising single crystals of these materials can be utilized in many different applications. As explained above, particularly advantageous results can be obtained in both tissue and contrast agent harmonic imaging. Although harmonic imaging has been performed in the past, harmonic-imaging performance was not optimal due to the bandwidth limits of the transducers. With transducers such as those described herein, however, one single transducer can be designed to do the job of two or more conventional PZT transducers.

The imaging of tissue generated harmonic responses can be improved by uniform harmonic response signal generation. An ultrasonic imaging system 100 in accordance with the present invention can produce harmonic response signals of greater magnitude in the far-field due to the relatively lower tissue attenuation at the lower transmit frequency. In the near-field, apodization of the wideband phased-array transducer 102, can be used to generate harmonic responses. Transmit apodization may weight a subset of the transducer's 102 elements more than another subset of elements. The effect of weighting a subset of the transducer's 102 elements is to increase waveform pressure in the near-field, while maintaining waveform pressure in the far-field. Often a hamming window is used to control the weighting of the various transducer 102 elements but a rectangular window, smaller than the actual aperture, has proven useful as well. As a result, transmit apodization can be employed to more quickly generate harmonic responses in the near-field.

Figure 7A:
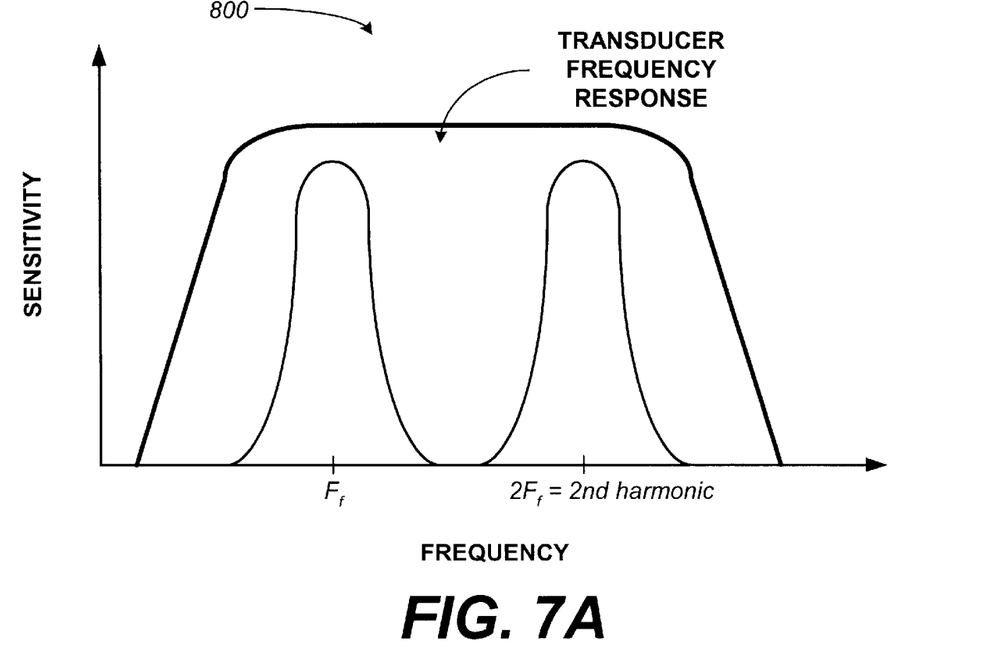
FIGS. 7A–7B illustrate the spectral response of typical wideband single crystal transducers that may be used for harmonic imaging of tissue and contrast agents with the ultrasonic imaging system of FIG. 1.
Figure 7B:
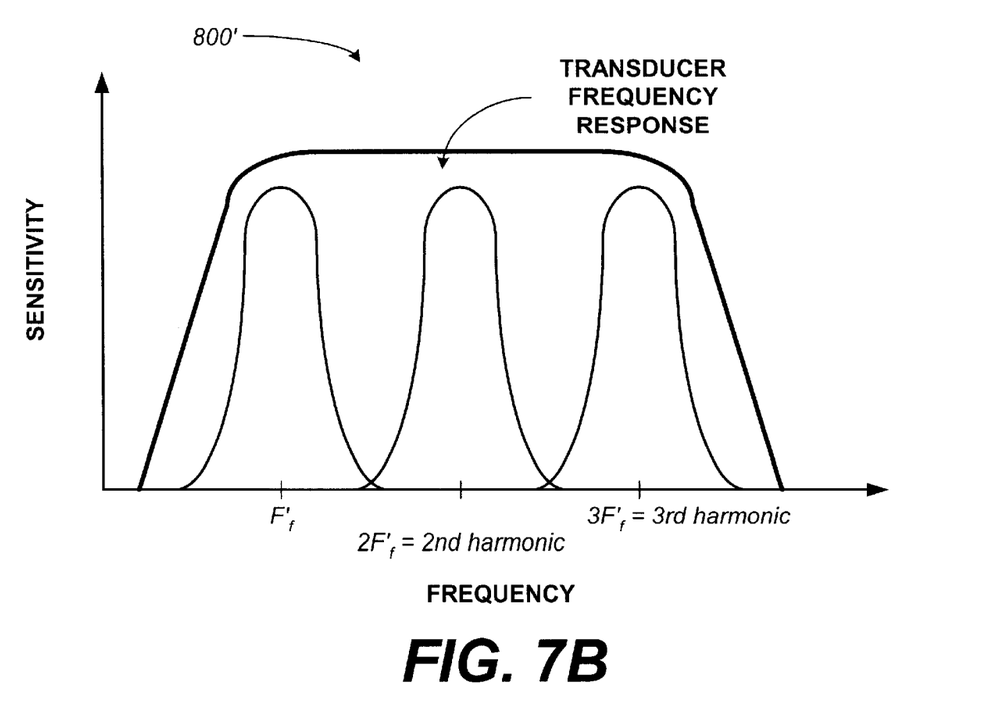

The shifting of the fundamental frequency of a transducer 102 in accordance with the present invention to very low frequencies, such as those below 1.5 MHz, is illustrated in FIGS. 7A and 7B. In this regard, FIG. 7A illustrates a graph showing a transducer frequency response 800 in accordance with harmonic imaging of a received second harmonic response. In the example shown in this figure, a low frequency pressure wave $F_f$ may be transmitted and a harmonic echo herein designated $2F_f$ may be received by the same transducer. Similarly, FIG. 7B illustrates a graph showing a transducer frequency response 800' having sufficient bandwidth to enable transmission at a relatively low fundamental frequency $F'_f$ and reception of harmonic echoes at both a second and a third harmonic frequency herein designated $2F'_f$ and $3F'_f$, respectively. Both harmonic echoes can be received at $2F'_f$ and $3F'_f$ simultaneously and then combined with proper gain control to form a mixed harmonic image. As is evident from this discussion, the extra bandwidth of single crystal transducers and MUTs provides an additional degree of freedom for processing harmonic response signals over a wide frequency range.

With such wide bandwidth, it may be advisable to avoid transmitting energy at the harmonic frequency because this energy can be confused with the harmonic signals returning to the transducer from the object or contrast agent being imaged. In particular, this overlap of signals can create unintended signal noise that will lower image quality. One solution to this problem is to simply filter the harmonic components of the transmitted signal so harmonics of the fundamental will not be transmitted by the transducer. An alternative to this solution is to utilize an arbitrary waveform generator, which controls the shape of the transmitted waveform such that its spectrum has very few harmonic components. As known in the art, it may also be advisable to cancel the fundamental received signals so that only harmonic signals are processed.

One method of accomplishing this cancellation is through pulse inversion. With this technique, the transducer is configured so as to fire multiple pulses that vary in phase. The received responses resulting from the multiple transmit pulses are received and stored. The received responses may then be mathematically manipulated as required (e.g., scaled and added) to remove the received fundamental components, thereby enhancing the non-linear components of the response signals at the harmonics.

Another method of accomplishing this cancellation is through amplitude modulation. With this technique, the transducer is fired to transmit pulses with various magnitudes. The received responses may then be mathematically manipulated as required (e.g., scaled and subtracted) to remove the received fundamental components, thereby enhancing the non-linear components of the response signals at the harmonics.

The additional bandwidth available from the described transducers can be particularly useful in contrast harmonic imaging. When imaging contrast agents, both the agents and the surrounding tissue generate harmonic signals. In that the tissue harmonic signals act to obscure the image of the contrast agent image, the tissue harmonic signals constitute noise that should be removed. It has been determined that when an ultrasound contrast agent is destroyed it emits broad bandwidth energy, while tissue only produces energy at the harmonics. Therefore, if a filter (e.g., a RF filter) is placed between the harmonics (e.g., between the second and third), the contrast agent bubble signal will not be obscured by the tissue noise signals.

It has been shown that contrast agents are destroyed more efficiently at lower frequencies of ultrasound. This phenomenon can be beneficial in many cases. For instance, it is possible to destroy the contrast agent bubbles and to correlate the reflow time with the blood flow of an organ of a patient. If a particular area of the organ fills in more quickly than another, the blood flow is higher in that particular area. Unfortunately, despite the benefit this technique provides, resolution may be sacrificed. One solution to this problem has been to destroy the contrast agent bubbles at a low frequency with a first transducer and receive the harmonics (at a higher frequency) with another transducer. Another solution to the problem was to use an existing transducer and live with results given the limited useful bandwidth of the transducer. However, as mentioned above, with the transducer of the present invention, a single transducer can replace two or more conventional transducers or in the case of a single transducer, enable significantly better imaging performance. For example, a single transducer constructed with the single crystal technology previously described herein can be used to transmit pressure waves at lower frequencies. Insonification with the lower frequency pressure waves provides better contrast agent destruction both in uniformity of contrast agent microbubble destruction through the tissue and in the magnitude of contrast agent microbubbles destroyed per pressure wave. Single crystal transducer technology also permits detection and measurement of higher order harmonics with the same transducer.

Because of bandwidth limitations created through use of conventional PZT-type materials, second and third harmonic signals have not been utilized to their full benefit. However, with the materials and techniques described herein, potentially even more advantageous imaging can be obtained by combining the second and the third harmonic signals. In that the second harmonic signal offers a better signal to noise ratio and the third provides better resolution, an improved image may be obtained when the two are combined. In such a combination, the third harmonic signal can be relied upon more heavily for the mid-field image to improve the shallow depth clutter noise, and far-field images can be imaged by relying upon the second harmonic signal more heavily for better penetration. As a result, multiple harmonic responses may be combined to produce a hybrid image having greatly improved resolution. As by way of a non-limiting example, an image may be generated from a combination of a portion of the fundamental responses and the second harmonic responses in the near field, a combination of second and third harmonics in the mid-field, and second harmonics in the far-field. The flexibility to combine and match all available harmonic responses to image the various fields or depths will provide for clearer ultrasonic imaging. Moreover, in that the two different images have different speckle patterns, these speckle patterns tend to cancel each other out, thereby producing an even clearer ultrasonic image.

While particular embodiments of the invention have been disclosed in detail in the foregoing description and drawings for purposes of example, it will be understood by those skilled in the art that variations and modifications thereof can be made without departing from the spirit and scope of the invention as set forth in the following claims.

Having thus described the invention, we claim at least the following:

1. A method for detecting an ultrasonic harmonic response of a contrast agent comprising:
   introducing at least one contrast agent into tissue targeted for imaging;
   insonifying the tissue with a pressure wave having a fundamental frequency of less than approximately 1.5 MHz to accomplish homogenous destruction of the at least one contrast agent; and
   measuring a non-integer harmonic response to the pressure wave, wherein the steps of insonifying and measuring are accomplished with a wideband phased-array transducer having a bandwidth comprising a transmit and a receive bandwidth and a center frequency, the bandwidth greater than 70 percent, where percent bandwidth comprises the difference between a high corner −6 dB frequency and a low corner −6 dB frequency, the difference divided by a center frequency of the transducer bandwidth.

2. The method of claim 1, further comprising:
   filtering the response with a radio-frequency (RF) filter such that tissue generated integer harmonic responses are removed.

3. The method of claim 1, wherein the transmit bandwidth is greater than approximately 25 percent, where percent transmit bandwidth comprises the difference between a high corner transmit −6 dB frequency and a low corner transmit −6 dB frequency, the difference divided by the transmit frequency.

4. The method of claim 1 wherein the receive bandwidth is greater than approximately 25 percent, where percent receive bandwidth comprises the difference between a high corner receive −6 dB frequency and a low corner receive −6 dB frequency, the difference divided by the receive frequency.

5. The method of claim 1 wherein substantially homogenous microbubble destruction is accomplished within a single pulse of a pulsed pressure wave.

6. The method of claim 1 wherein the transmitted pressure wave is generated such that the wideband phased-array transducer detects less energy due to the transmitted pressure wave in the receive bandwidth than from harmonic responses within the receive bandwidth.

7. The method of claim 1 wherein the transmitted pressure wave comprises a multi-pulsed signal to cancel the effects of transmitted energy within the receive bandwidth.

8. The method of claim 1 wherein substantially homogenous microbubble destruction is accomplished after a first pulse of a multi-pulsed ultrasound signal.

9. The method of claim 1 wherein microbubble destruction is enhanced by abruptly changing the envelope of the pressure wave.

10. An ultrasonic imaging system for harmonic imaging of one or more contrast agents in an object in a medium comprising:
    a transmitter for generating ultrasound signals wherein the fundamental frequency is less than approximately 1.5 MHz;
    a wideband phased-array transducer capable of converting the ultrasound signals from the transmitter into acoustic pressure waves, said transducer further capable of receiving and converting at least one non-integer harmonic acoustic response from the transmitted acoustic pressure waves into at least one response signal;
    a receiver for detecting the at least one non-integer harmonic acoustic response from the at least one response signal;
    a control system electrically coupled to said transmitter and said receiver, said control system used to control the operation of said transmitter and said receiver;
    a video processor for converting the at least one response signal to a display signal; and
    a monitor for converting the display signal into an image, wherein the phased-array transducer has a bandwidth of greater than approximately 70 percent, where percent bandwidth comprises the difference between a high corner −6 dB frequency and a low corner −6 dB frequency, the difference divided by a center frequency of the transducer bandwidth.

11. The system of claim 10 wherein the phased-array transducer has a transmit bandwidth of greater than approximately 25 percent, where percent transmit bandwidth comprises the difference between a high corner transmit −6 dB frequency and a low corner transmit −6 dB frequency, the difference divided by the transmit frequency.

12. The system of claim 11 wherein a radio frequency (RF) filter removes tissue reflected integer harmonic responses.

13. The system of claim 12 wherein the transmitter generates a pulsed ultrasound signal with an abrupt change in its envelope for enhancing microbubble destruction.

14. The system of claim 10 wherein the phased-array transducer has a receive bandwidth of greater than approximately 25 percent, where percent receive bandwidth comprises the difference between a high corner receive −6 dB frequency and a low corner receive −6 dB frequency, the difference divided by the receive frequency.

15. The system of claim 14 wherein the transmitter generates an ultrasound signal having less energy in the receive bandwidth than that energy received by the wideband phased-array transducer from harmonic responses within the receive bandwidth.

16. The system of claim 14 wherein the transmitter generates a multi-pulse ultrasound signal to cancel the effects of transmitted energy within the receive bandwidth.

17. The system of claim 10 wherein substantially homogenous microbubble destruction is accomplished within a single pulse of a pulsed ultrasound signal.

18. The system of claim 10 wherein substantially homogenous microbubble destruction is accomplished after a first pulse of a multi-pulsed ultrasound signal.

19. A wideband phased-array transducer capable of converting an input ultrasound signal of a frequency less than approximately 1.5 MHz into an acoustic pressure wave, said transducer configured to receive and convert at least one harmonic acoustic response from the transmitted acoustic pressure wave into at least one response signal, wherein said transducer having a bandwidth comprising a transmit and a receive bandwidth and a center frequency, the bandwidth being greater than approximately 70 percent, where percent bandwidth comprises the difference between a high corner −6 dB frequency and a low corner −6 dB frequency, the difference divided by the center frequency.

20. The transducer of claim 19 wherein the transmit bandwidth is greater than 25 percent, where percent transmit bandwidth comprises the difference between a high corner transmit −6 dB frequency and a low corner transmit −6 dB frequency, the difference divided by the transmit frequency.

21. The transducer of claim 19 wherein the receive bandwidth is greater than 25 percent, where percent receive bandwidth comprises the difference between a high corner receive −6 dB frequency and a low corner receive −6 dB frequency, the difference divided by the receive frequency.

22. The transducer of claim 19 wherein the element array comprises at least two matching layers.

23. The transducer of claim 19 wherein the element array comprises at least three matching layers.

24. The transducer of claim 19 wherein the element array is constructed of materials comprising a single crystal.

25. The transducer of claim 19 wherein the transducer is a micro-machined ultrasonic transducer (MUT).

26. An ultrasonic imaging system for harmonic imaging of one or more contrast agents in an object in a medium comprising:
    means for insonifying the tissue with a pressure wave having a fundamental frequency of less than approximately 1.5 MHz to accomplish substantially homogenous destruction of the at least one contrast agent;
    means for measuring a harmonic response to the pressure wave;
    means for processing the measured non-integer harmonic response such that harmonic tissue generated responses are removed from the measured harmonic response; and
    means for converting the processed harmonic response for display, wherein the means for insonifying and the means for measuring a harmonic response are accomplished with a wideband phased-array transducer.

27. The system of claim 26 wherein the transducer has a bandwidth comprising a transmit and a receive bandwidth and a center frequency, the bandwidth greater than approximately 70 percent, where percent bandwidth comprises the difference between a high corner −6 dB frequency and a low corner −−6 dB frequency, the difference divided by a center frequency of the transducer bandwidth.

28. The system of claim 26 further comprising:
    means for canceling the effects of transmitted energy within the receive bandwidth.

29. The system of claim 26 wherein the means for insonifying accomplishes microbubble destruction within a single pulse of a pulsed pressure wave.

30. The system of claim 26 wherein the means for insonifying accomplishes microbubble destruction by abruptly changing the envelope of a pressure wave.

31. A method for detecting an ultrasonic harmonic response comprising:
  insonifying with a pressure wave having a fundamental frequency of less than approximately 1.5 MHz to develop a more uniform far-field harmonic response;
  using transducer apodization to generate a near-field harmonic response; and
  measuring a harmonic response to the pressure wave, wherein the method steps are accomplished with a wideband phased-array transducer having a bandwidth comprising a transmit and a receive bandwidth and a center frequency, the bandwidth greater than approximately 70 percent, where percent bandwidth comprises the difference between a high corner −6 dB frequency and a low corner −6 dB frequency, the difference divided by a center frequency of the transducer bandwidth.

32. The method of claim 31 wherein transducer apodization is accomplished with a hamming window.

33. The method of claim 31 wherein transducer apodization is accomplished by controllably firing a subset of transducer elements.

34. The method of claim 33 wherein the subset of transducer elements forms a rectangle.

35. The method of claim 31 wherein the transmit bandwidth is greater than approximately 25 percent, where percent transmit bandwidth comprises the difference between a high corner transmit −6 dB frequency and a low corner transmit −6 dB frequency, the difference divided by the transmit frequency.

36. The method of claim 31 wherein the receive bandwidth is greater than approximately 25 percent, where percent receive bandwidth comprises the difference between a high corner receive −6 dB frequency and a low corner receive −6 dB frequency, the difference divided by the receive frequency.

37. The method of claim 31 wherein the transmitted pressure wave is generated such that the wideband phased-array transducer detects less energy due to the transmitted pressure wave in the receive bandwidth than from harmonic responses within the receive bandwidth.

38. The method of claim 31 wherein the transmitted pressure wave comprises a multi-pulsed signal to cancel the effects of transmitted energy within the receive bandwidth.

39. A method for detecting an ultrasonic harmonic response comprising:
  insonifying a tissue of interest with a pressure wave having a fundamental frequency of less than approximately 1.5 MHz; and
  measuring at least one integer harmonic response to the pressure wave, wherein the steps of insonifying and measuring are accomplished with a wideband phased-array transducer having a bandwidth comprising a transmit and a receive bandwidth and a center frequency, the bandwidth greater than 70 percent, where percent bandwidth comprises the difference between a high corner −6 dB frequency and a low corner −6 dB frequency, the difference divided by a center frequency of the transducer bandwidth.

40. The method of claim 39, further comprising:
  filtering the response with a radio-frequency (RF) filter such that non-integer harmonic responses are removed.

41. The method of claim 39, wherein the transmit bandwidth is greater than approximately 25 percent, where percent transmit bandwidth comprises the difference between a high corner transmit −6 dB frequency and a low corner transmit −6 dB frequency, the difference divided by the transmit frequency.

42. The method of claim 39 wherein the receive bandwidth is greater than approximately 25 percent, where percent receive bandwidth comprises the difference between a high corner receive −6 dB frequency and a low corner receive −6 dB frequency, the difference divided by the receive frequency.

43. The method of claim 39 wherein the transmitted pressure wave is generated such that the wideband phased-array transducer detects less energy due to the transmitted pressure wave in the receive bandwidth than from harmonic responses within the receive bandwidth.

44. The method of claim 39 wherein the transmitted pressure wave comprises a multi-pulsed signal to cancel the effects of transmitted energy within the receive bandwidth.

45. An ultrasonic imaging system for harmonic imaging of one or more objects in a medium comprising:
  a transmitter for generating ultrasound signals wherein the fundamental frequency is less than approximately 1.5 MHz;
  a wideband phased-array transducer capable of converting the ultrasound signals from the transmitter into acoustic pressure waves, said transducer further capable of receiving and converting at least one integer harmonic acoustic response from the transmitted acoustic pressure waves into at least one response signal;
  a receiver for detecting the at least one integer harmonic acoustic response from the at least one response signal;
  a control system electrically coupled to said transmitter and said receiver, said control system used to control the operation of said transmitter and said receiver wherein said control system is configured to perform transducer apodization to generate a near-field integer harmonic response;
  a video processor for converting the at least one response signal to a display signal; and
  a monitor for converting the display signal into an image, wherein the phased-array transducer has a transmit and receive bandwidth of greater than approximately 70 percent, where percent bandwidth comprises the difference between a high corner −6 dB frequency and a low corner −6 dB frequency, the difference divided by a center frequency of the transducer bandwidth.

46. The system of claim 45 wherein the phased-array transducer has a transmit bandwidth of greater than approximately 25 percent, where percent transmit bandwidth comprises the difference between a high corner transmit −6 dB frequency and a low corner transmit −6 dB frequency, the difference divided by the transmit frequency.

47. The system of claim 45 wherein the phased-array transducer has a receive bandwidth of greater than approximately 25 percent, where percent receive bandwidth comprises the difference between a high corner receive −6 dB frequency and a low corner receive −6 dB frequency, the difference divided by the receive frequency.

48. The system of claim 47 wherein the transmitter generates a transmitted pressure wave that has less energy in the receive bandwidth than that energy received by the wideband phased-array transducer from harmonic responses within the receive bandwidth.

49. The system of claim 47 wherein the transmitter generates a multi-pulse ultrasound signal to cancel the effects of transmitted energy within the receive bandwidth.

50. The system of claim 45 wherein a radio frequency (RF) filter removes non-integer harmonic responses.

51. The system of claim 45 wherein the control system accomplishes transducer apodization with a hamming window.

52. The system of claim 45 wherein the control system accomplishes transducer apodization by controllably firing a subset of transducer elements.

53. The system of claim 52 wherein the subset of transducer elements forms a rectangle.

54. An ultrasonic imaging system for harmonic imaging of one or more objects and one or more contrast agents in a medium comprising:

a transmitter for generating ultrasound signals wherein the fundamental frequency is less than approximately 1.5 MHz;

a wideband phased-array transducer capable of converting the ultrasound signals from the transmitter into acoustic pressure waves, said transducer further capable of receiving and converting at least one harmonic acoustic response from the transmitted acoustic pressure waves into at least one response signal;

a receiver for detecting the at least one harmonic acoustic response from the at least one response signal to generate at least one integer harmonic response generated from tissue, the receiver further configured to receive at least one non-integer harmonic response signal generated by the at least one contrast agent; and a control system electrically coupled to said transmitter and said receiver, said control system used to control the operation of said transmitter and said receiver wherein said control system is configured to perform transducer apodization to generate a near-field harmonic response, the control system further configured to permit operator selection of at least one operating mode selected from the group consisting of a contrast agent imaging mode and a tissue imaging mode;

a video processor for converting the at least one response signal to a display signal; and a monitor for converting the display signal into an image, wherein the phased-array transducer has a transmit and receive bandwidth of greater than approximately 70 percent, where percent bandwidth comprises the difference between a high corner −6 dB frequency and a low corner −6 dB frequency, the difference divided by a center frequency of the transducer bandwidth.

55. The system of claim 54 wherein the phased-array transducer has a transmit bandwidth of greater than approximately 25 percent, where percent transmit bandwidth comprises the difference between a high corner transmit −6 dB frequency and a low corner transmit −6 dB frequency, the difference divided by the transmit frequency.

56. The system of claim 54 wherein the phased-array transducer has a receive bandwidth of greater than approximately 25 percent, where percent receive bandwidth comprises the difference between a high corner receive −6 dB frequency and a low corner receive −6 dB frequency, the difference divided by the receive frequency.

57. The system of claim 56 wherein the transmitter generates a transmitted pressure wave that has less energy in the receive bandwidth than that energy received by the wideband phased-array transducer from harmonic responses within the receive bandwidth.

58. The system of claim 56 wherein the transmitter generates a multi-pulse ultrasound signal to cancel the effects of transmitted energy within the receive bandwidth.

59. The system of claim 54 wherein a radio frequency (RF) filter removes non-integer harmonic responses.

60. The system of claim 54 wherein the control system accomplishes transducer apodization with a hamming window.

61. The system of claim 54 wherein the control system accomplishes transducer apodization by controllably firing a subset of transducer elements.

62. The system of claim 61 wherein the subset of transducer elements forms a rectangle.

* * * * *